US012629405B2

(12) United States Patent
Nesselhut et al.

(10) Patent No.: US 12,629,405 B2
(45) Date of Patent: May 19, 2026

(54) EZRIN PEPTIDE 1 FOR USE IN A METHOD OF TREATING COVID-19

(71) Applicant: PANTAPHARM AG, Duderstadt (DE)

(72) Inventors: Thomas Nesselhut, Duderstadt (DE);
Jan Nesselhut, Duderstadt (DE);
Rüdiger Osmers, Duderstadt (DE)

(73) Assignee: PANTAPHARM AG, Duderstadt (DE)

( * ) Notice: Subject to any disclaimer, the term of this patent is extended or adjusted under 35 U.S.C. 154(b) by 737 days.

(21) Appl. No.: 17/915,847

(22) PCT Filed: Mar. 31, 2021

(86) PCT No.: PCT/EP2021/058459
§ 371 (c)(1),
(2) Date: Sep. 29, 2022

(87) PCT Pub. No.: WO2021/198346
PCT Pub. Date: Oct. 7, 2021

(65) Prior Publication Data
US 2024/0226231 A1      Jul. 11, 2024

(30) Foreign Application Priority Data

| | | |
|---|---|---|
| Apr. 1, 2020 | (EP) ..................................... | 20167623 |
| Apr. 30, 2020 | (EP) ..................................... | 20172561 |
| May 11, 2020 | (EP) ..................................... | 20173939 |

(51) Int. Cl.
*A61K 38/17*      (2006.01)
*A61K 9/00*      (2006.01)
*A61P 31/14*      (2006.01)

(52) U.S. Cl.
CPC ........ *A61K 38/1703* (2013.01); *A61K 9/0019* (2013.01); *A61P 31/14* (2018.01)

(58) Field of Classification Search
CPC ..... A61K 38/1703; A61K 38/00; A61P 31/14; C07K 14/4735
See application file for complete search history.

(56) References Cited

U.S. PATENT DOCUMENTS

| | | | |
|---|---|---|---|
| 6,849,596 B1 | 2/2005 | Holms | |
| 2016/0346383 A1 | 12/2016 | Holms et al. | |
| 2024/0180999 A1 | 6/2024 | Nesselhut et al. | |

FOREIGN PATENT DOCUMENTS

| | | | | |
|---|---|---|---|---|
| WO | WO-9533768 A1 | * | 12/1995 | ........... C07K 14/005 |
| WO | 2004067024 A2 | | 8/2004 | |
| WO | 2007060440 A2 | | 5/2007 | |

OTHER PUBLICATIONS

Holms, Rupert Donald. "The COVID-19 cell signalling problem: Spike, RAGE, PKC, p38, NFκB & IL-6 Hyper-expression and the human ezrin peptide, VIP, PKA-CREB solution." Immuno 2.2 (2022): 260-282. (Year: 2022).*
Bolognesi, Benedetta, et al. "Single point mutations induce a switch in the molecular mechanism of the aggregation of the Alzheimer's disease associated AB42 peptide." ACS Chemical Biology 9.2 (2014): 378-382. (Year: 2014).*
Sawai, Monali V., et al. "Impact of single-residue mutations on the structure and function of ovispirin/novispirin antimicrobial peptides." Protein engineering 15.3 (2002): 225-232. (Year: 2002).*
Wang, Xiaoling, et al. "Potential aggregation prone regions in biotherapeutics: a survey of commercial monoclonal antibodies." MAbs. vol. 1. No. 3. Taylor & Francis, 2009. (Year: 2009).*
Millet, Jean Kaoru, et al. "Ezrin interacts with the SARS coronavirus Spike protein and restrains infection at the entry stage." PLoS One 7.11 (2012): e49566. (Year: 2012).*
Anonymous , "Ezrin Peptide (HEP-1) for Treatment of Coronavirus Disease (COVID-19) Infection", https://clinicaltrials.gov/ct2/show/NCT04627233, 4 pages (Nov. 13, 2020).
Bessler, W , "Arbeitsgruppe Vakzine", http://web.archive.org/web/20200601141608/https://sites.google.com/site/alsanafreiburg/home/ak-vakzine, 23 pages, (Mar. 24, 2020). [Non-English].
Holms, R , et al., "Review of Russian ezrin peptide treatment of acute viral respiratory disease and virus induced pneumonia; a potential treatment for covid-19", https://www.researchgate.net/publication/340600041_Review_of_Russian_ezrin_peptide_treatment_of_acute_viral_respiratory_disease_and_virus_induced_pneumonia_a_potential_treatment_for_covid-19, 42 pages, (Apr. 12, 2020).
Mehta, P , et al., "COVID-19: consider cytokine storm syndromes and immunosuppression", The Lancet 395, 1033-1034 (2020).
Millet, J , et al., "Ezrin Interacts with the SARS Coronavirus Spike Protein and Restrains Infection at the Entry Stage", PLoS ONE 7 (11), e49566, 1-13 (2012).
Nalbandian, A , et al., "Post-acute COVID-19 syndrome", Nature Medicine 27, 601-615 (2021).
Peters, J , et al., "Akuttherapie von Viruskrankheiten", https://jimdo-storage.global.ssl.fastly.net/file/79973013-b216-4ade-bc96-b1a4ecfb8a3b/Peters_Akuttherapie_von_Viruskrankheiten.pdf, 3 pages (Mar. 24, 2020). [Non-English].
Van Kampen, J , et al., "Shedding of infectious virus in hospitalized patients with coronavirus disease-2019 (COVID-19): duration and key determinants", https://www.medrixiv.org/content/10.1101/2020.06.0820125310v1.full.pdf, 28 pages (2020).
Al-Aly, et al., "High-dimensional characterization of post-acute sequelae of COVID-19", Nature 594, 259-264 (2021).
British Heart Foundation, "Long Covid: symptoms, tests, treatment and support", https://www.bhf.org.uk/informationsupport/heart-matters-magazine/news/coronavirus-and-your-health/long-covid, 6 pages (May 10, 2023).
Davis, et al., "Characterizing long COVID in an international cohort: 7 months of symptoms and their impact", EClinical Medicine 38, 101019, 19 pages (2021).
Lopez-Leon, et al., "More than 50 long-term effects of COVID-19: a systematic review and meta-analysis", Scientific Reports 11, 16144, 12 pages (2021).
Ludvigsson, J , "Case report and systematic review suggest that children may experience similar long-term effects to adults after clinical COVID-19", Acta Paediatrica 110, 914-921 (2021).

(Continued)

*Primary Examiner* — Lianko G Garyu
*Assistant Examiner* — David Paul Bowles
(74) *Attorney, Agent, or Firm* — Viksnins Harris Padys Malen LLP

(57)      ABSTRACT

The present invention relates to Ezrin peptide 1 and/or an analogue thereof for use in a method of treating COVID-19 and for use in a method of treating post COVID-19 syndrome.

18 Claims, No Drawings

Specification includes a Sequence Listing.

(56)          References Cited

OTHER PUBLICATIONS

Patent Cooperation Treaty, International Search Report and Written Opinion for PCT/EP2021/058459, 33 pages, dated Sep. 24, 2021.
Patent Cooperation Treaty, International Search Report and Written Opinion for PCT/EP2022/058622, 27 pages, dated Jun. 7, 2022.
Tenforde, et al., "Symptom Duration and Risk Factors for Delayed Return to Usual Health Among Outpatients with COVID-19 in a Multistate Health Care Systems Network—United States, Mar.-Jun. 2020", MMWR, Morbidity and Mortality Weekly Report 69 (30), 993-998 (2020).
Thaller, A, "Was steht auf dem Spielplan im Welt-Theater ? Corona", https://jimdo-storage.global.ssl.fastly.net/file/73db2b70-e5cl-471f-bb9e-13d7830f1501/Corona-Theater%2011-2021.pdf, 10 pages (2022). [Non-English].
Yelin, et al., "Long-Term consequences of COVID-19: research needs", The Lancet, Infectious Diseases 20 (10), 1115-1117 (2020).

\* cited by examiner

EZRIN PEPTIDE 1 FOR USE IN A METHOD OF TREATING COVID-19

SEQUENCE LISTING

The instant application contains a Sequence Listing that has been submitted electronically in ASCII format and is hereby incorporated by reference in its entirety. Said ASCII copy, created on Jul. 24, 2023, is named 05710_059 US1_SL.txt and is 2,343 bytes in size.

The present invention concerns Ezrin peptide 1 for use in a method of treating COVID-19.

Coronavirus disease 2019 (COVID-19) is caused by a novel coronavirus called SARS-CoV-2. The acronym "SARS" stands for severe acute respiratory syndrome. An outbreak of COVID-19 in the Hubei province (China) at the end of 2019 is spreading globally and is impacting the health of people and of the economy worldwide. As of Mar. 30, 2020, COVID-19 has been confirmed in about 750,000 people worldwide, carrying a mortality of approximately 3-5%, compared with a mortality rate of less than 1% from influenza. Most diagnosis relies on PCR using specimens from the respiratory tract.

On 11 Mar. 2020, the Director-General of WHO declared the spate of infections caused by SARS-COV-2 (COVID-19) a pandemic.

The novel coronavirus SARS-COV-2 causes flu-like symptoms such as dry cough, fever, a runny nose and fatigue. There have also been reports of an itchy throat, headaches, joint pains, nausea, diarrhoea and shivering. The virus spreads from person to person. Droplet infection is the main mode of transmission. Transmission can take place directly, from person-to-person, or indirectly through contact between hands and the mucous membranes of the mouth, the nose or the conjunctiva of the eyes. There have been reports of persons who were infected by individuals who had only shown slight or non-specific symptoms of disease. The percentage of asymptomatic cases is unclear. It is currently thought that an infected person can go up to 14 days before noticing any symptoms. According to WHO, the incubation period is, on average, five to six days.

Among the cases reported to date, in three out of five cases infection was mild with symptoms, e.g. dry cough and fever less than 39.5° C., for about 1 week. This means that not all diseases that follow a SARS-COV-2 infection take a serious course and require treatment. Unlike other acute infectious diseases progressing to sepsis, the severe courses of COVID-19 seemingly show prolonged progression from onset of first symptoms to life-threatening deterioration of (primarily) lung function including difficult breathing and pneumonia. Severe acute respiratory distress syndrome (ARDS) reflects the hallmark of a critical course of the disease. Treatment of the infection depends on the severity of the disease presentation (e.g. administering oxygen, maintaining fluid balance, if necessary administering antibiotics to combat bacterial co-infections) and also includes the treatment of relevant underlying chronic illnesses. Current management of COVID-19 is supportive and ARDS is the leading cause of mortality.

Accumulating evidence suggests that a subgroup of patients with severe COVID-19 might have a cytokine storm syndrome which leads to hyper-inflammation and irremediable lung tissue damage. It has been reported that a cytokine profile resembling sHLH (secondary haemophagocytic lymphohistiocytosis) is associated with COVID-19 disease severity, characterized by increased interleukin (IL-)2, IL-7, granulocyte-colony stimulating factor, interferon-γ inducible protein 10, monocyte chemo-attractant protein 1, macrophage inflammatory protein 1-α, and tumour necrosis factor-α. Predictors of fatality from a recent retrospective, multicentre study of 150 confirmed COVID-19 cases in Wuhan, China, included elevated ferritin (mean 1297.6 ng/ml in non-survivors vs 614.0 ng/ml in survivors; p<0.001) and IL-6 (p<0.0001), suggesting that mortality might be due to virally driven hyper-inflammation (Mehta et al., The Lancet, Vol. 395, p. 1033-1034 (March 2020)).

During the course of the COVID-19 pandemic, it has also become apparent that patients with COVID-19 suffer from late/long-term effects long after the acute infection has subsided. Although those affected have recovered from COVID-19 itself, they are by no means healthy. Instead, they suffer long-term effects such as chronic fatigue, breathing difficulties, such as shortness of breath, loss of smell, concentration difficulties, anxiety, and depression. These long-term symptoms are also termed post-COVID-19 syndrome, long COVID or late COVID.

There is an urgent need for an effective treatment of COVID-19. The current focus has been on the development of novel therapeutics, including anti-viral agents and vaccines. However, it may take at least several months, in the worst case more than 1 year, until a suitable new medication and a vaccine has been developed. Until then there is an urgent need for the prevention and/or treatment of ARDS, including hyper-inflammation, as a complication of COVID-19 using existing, approved therapies with proven safety profiles to address the immediate need to reduce the rising mortality.

The inventors have found out that Ezrin peptide 1 or a pharmaceutical composition comprising Ezrin peptide 1 and a pharmaceutically acceptable carrier is suitable for avoiding a critical course of the COVID-19 disease.

The inventors have also found out that analogues of Ezrin peptide 1 or a pharmaceutical composition comprising an analogue of Ezrin peptide 1 and a pharmaceutically acceptable carrier is suitable for avoiding a critical course of the COVID-19 disease.

The inventors have also found out that combinations of Ezrin peptide 1 and an analogue of Ezrin peptide 1 or a pharmaceutical composition comprising Ezrin peptide 1, an analogue of Ezrin peptide 1 and a pharmaceutically acceptable carrier is suitable for avoiding a critical course of the COVID-19 disease.

The inventors have also found out that Ezrin peptide 1, the analogues of Ezrin peptide 1 and pharmaceutical compositions comprising Ezrin peptide 1 or an analogue of Ezrin peptide 1 or a combination of Ezrin peptide 1 with an analogue of Ezrin peptide 1 and a pharmaceutically acceptable carrier are suitable for healing or at least ameliorating post-COVID-19 syndrome and also for reducing the risk of patients to suffer from post-COVID-19 syndrome.

Ezrin protein, also known as cryptocillin or villin-2, is a protein encoded in humans by the EZR gene. The peptide used for the present invention comprises or is a pharmaceutical tetradecapeptide NH2_Thr-Glu-Lys-Lys-Arg-Arg-Glu-Thr-Val-Glu-Arg-Glu-Lys-Glu_COOH (SEQ ID NO:1), comprising 14 amino acid residues, which is known as HEP-1 peptide or human Ezrin peptide one (TEKKRRETVEREKE; SEQ ID NO: 1) and which was developed for the treatment of HIV-infection (WO 95/33768 A1). HEP-1 is known to have anti-viral hepatitis C biological activity and can be used for the treatment of the patients with hepatitis C (WO 2004/067024 A2). It has been additionally reported that HEP-1 has antiulcer biological activity and can be used for the treatment of ulcer diseases of the gastrointestinal tract (WO 2007/060440).

The analogues of Ezrin peptide 1 are tetradecapeptides, which are of the following general formula:

```
(I)
NH2_X¹-Glu-Lys-Lys-Arg-Arg-Glu-Thr-Val-Glu-Arg-
Glu-X²-X³_COOH
```

SEQ ID NO:5 where X¹, X² and X³ are identical or different and are non-polar amino acid residues, where the amino acids are in particular selected from the group consisting of glycine, alanine, valine, leucine, methionine, isoleucine, proline, phenylalanine, tryptophan and combinations thereof. A particular example of such an analogues of Ezrin peptide 1 is the compound of formula (I), where X¹, X² and X³ are glycine residues, i.e. the compound of sequence NH2_Gly-Glu-Lys-Lys-Arg-Arg-Glu-Thr-Val-Glu-Arg-Glu-Gly-Gly_COOH (SEQ ID NO:2). The analogues of Ezrin peptide 1 of the formula (I) are known from US 2016/0346383.

The peptides used in the present invention, i.e. Ezrin peptide 1 and its analogues of formula (I) can be synthesized by peptide synthetic chemistry well known in the art, e.g. from US 2016/0346383 and the references cited therein. For example, the peptides of the invention can be synthesized by liquid-phase synthesis using standard procedure or by solid-phase synthesis or by combinations thereof. When solid-phase synthesis is employed, then a solid phase is used, such as polystyrene resin or polyamide resin, or PEG hybrid polystyrene resin, or resin based on PEG. Different protective groups are used during the synthesis, for example, N-terminal protecting groups, t-Boc or FMOC protective groups. In some instances, fragments may be synthesized using solid-state methods and then coupled together in solution. Peptides can be synthesized from the carbonyl group side to amino group side of the amino acid chain in this method, although peptides are synthesized in the opposite direction in cells. In such methods, an amino-protected amino acid is bound to a substrate bead (i.e. a resin bead) forming a covalent bond between the carbonyl group and the resin. The amino group is then de-protected and reacted with the carbonyl group of the next amino-protected amino acid. The cycle is repeated as often as required in order to form the desired peptide chain. The synthesized peptide is then cleaved from the bead at the end of the procedure. The protecting groups for the amino groups mostly used in this peptide synthesis are 9-fluorenylmethyloxycarbonyl group ("Fmoc") and t-butyloxycarbonyl ("Boc"). The Fmoc group is removed from the amino terminus with base while the Boc group is removed with acid. Moreover, benzyloxycarbonyl (Z) groups or allyloxycarbonyl (Alloc) protective groups, or photo-removable (lithographic) protective groups, or side group protection technique may be employed. Peptide products are purified by HPLC separation or by any other purification method. Peptide structure is confirmed by amino acid analysis, mass spectrometry, and high performance liquid chromatography data. The peptide used in the present invention has preferably the amino acid sequence as shown above but may also be modified (for example at the C or N terminals) to protect them from degradation or to increase their bioavailability and/or biocompatibility, as deemed suitable or required by the skilled person.

"Subject" or "patient" as used herein refers to humans tested positive for SARS-COV-2 or suspected of being infected with SARS-COV-2. These subjects may be affected by Coronavirus disease 2019 (COVID-19) or are being suspected of developing Coronavirus disease 2019 (COVID-19). As mentioned above, COVID-19 is caused by a novel coronavirus called SARS-COV-2.

COVID-19 as used herein is associated with one or more of the following symptoms: dry cough, fever, a runny nose, fatigue, itchy throat, headaches, joint pains, nausea, diarrhoea and shivering. In particular, COVID-19 is reported to be associated as main symptoms with dry cough, breathing symptoms, fever and fatigue.

It is reported that the median disease duration of COVID-19 in a patient with mild symptoms is 1-2 weeks. Severe courses may include hospitalization and intensive care for about 3-6 weeks.

The pharmaceutical compositions used for the invention may comprise optionally other pharmaceutically active substances, such as anti-viral, anti-bacterial, analgesic and/or anti-inflammatory substances. In a preferred embodiment, the pharmaceutical composition may also contain immune-stimulatory agents. Examples for anti-viral substances are acyclovir, ribavirin, valaciclovir, oseltamivir, remdesivir or zanamivir. Examples for anti-bacterial substances are antibiotics including those of the classes aminoglycosides, ansamycins, carbacephems, cephalosporins, glycopeptides, macrolides, penicillins, polypeptides, quinolones, sulfonamides, tetracyclines, glycylcyclines, oxazolidinones, amphenicols, pleuromutilins, lincosamides, streptogramins, steroid antibacterials, cyclopeptides lipopeptides, and mixtures thereof.

The term "about" as used herein, means in quantitative terms plus or minus 5%, or in another embodiment plus or minus 10%, or in another embodiment plus or minus 15%, or in another embodiment plus or minus 20%. In particular, the term "about" as used herein, means in quantitative terms plus or minus 5% or the respective value given.

"Pharmaceutically acceptable" is meant to encompass any carrier, which does not interfere with the effectiveness of the biological activity of the active ingredients and that is not toxic to the patient to whom it is administered. Examples of suitable pharmaceutical carriers are well known in the art and include phosphate buffered saline solutions, water, emulsions, such as oil/water emulsions, various types of wetting agents, sterile solutions etc. Such carriers can be formulated by conventional methods and can be administered to the subject at an effective dose. Additional pharmaceutically compatible carriers can include gels, bioabsorbable matrix materials, implantation elements containing the therapeutic agent, or any other suitable vehicle, delivery or dispensing means or material(s).

The dosage of the pharmaceutical composition is determined by the physician on the basis of the patient-specific parameters, such as age, weight, sex, severity of the disease, etc. The terms "dosage regimen" or "mode of treatment" refer to a timely sequential or simultaneous administration of the Ezrin peptide 1 or its analogue or a combination thereof, and any other optional pharmaceutically active substance. This means that the components may be provided in a unit dosage form with physical contact to each other (e.g. one single tablet or solution) or as separate entities (e.g. two tablets or solutions) to be taken simultaneously or with a certain time difference. This time difference may be in the range of 0.5 hour and 1 day, preferably between 1 hour and 5 hours.

The dosage of Ezrin peptide 1 and its analogues is not particularly critical, as Ezrin peptide 1 and its analogues are not toxic even at high dosages of 50 mg per kg body weight per day or higher. Preferably, Ezrin peptide 1 and its analogues are administered to an adult human in an amount of at least 0.1 mg per day, in particular at least 0.2 mg per day, e.g. in an amount of at least 0.5 mg per day, such as 0.1 to 50 mg per day or 0.2 to 20 mg per day or 0.5 to 10 mg per day. Typically for parental administrations lower dosages will be required than for oral or rectal administration. To achieve a rapid relief of the symptoms of COVID-19 it may be reasonable to administer at least 1 mg per day or at least 2 mg per day but in other cases a lower dosage may be suitable.

In one embodiment, the Ezrin peptide 1 is administered in a dosage in the range of or between about 0.2 and 8 milligrams (mg), preferably 1 to 5 mg, more preferably 2 to 4 mg per day. In another embodiment, the Ezrin peptide 1 is administered in a dosage in the range of 0.1 and 5 milligrams per day (mg/d), preferably 0.1 to 4 mg/d, more preferably 0.1 to 1 mg/d, especially 0.1 to 0.5 mg/d. It is also possible to start with higher dosage of e.g. in the range of 1 to 5 mg/d, more preferably 1 to 3 mg/d and then continue with lower dosage of e.g. 0.1 to 0.5 mg/d.

The Ezrin peptide 1 and/or an analogue thereof, such as the pharmaceutical composition comprising Ezrin peptide 1 and/or an analogue thereof may be administered to the subject prior to, during and after symptoms associated with COVID-19 are present. Preferably, it is administered immediately after the onset of at least one symptom associated with COVID-19. If this is not possible it should be preferably administered after a positive test result for SARS-COV-2 infection has been received. If this is not possible it should be administered prior to or immediately after the onset of fever, cough and/or breathing problems. The Ezrin peptide 1 or the pharmaceutical composition comprising Ezrin peptide 1 should be preferably administered prior to the start of the hospitalization of the patient. As a general rule: the earlier, the better. The dosage may be administered in one portion daily or in several partial doses over the day or every second day. The administration should be made during the course of the infection and be maintained until the last of the symptoms associated with COVID-19 has disappeared for at least 1 day, better 2 days. The Ezrin peptide 1 and/or an analogue thereof, such as the pharmaceutical composition comprising Ezrin peptide 1 and/or an analogue thereof may also be administered prophylactically, e.g. before an infection may occur, for example 1 or 2 days before an infection may occur.

The pharmaceutical composition may be prepared and administered in any dosage form suitable for administration to the subject's body. It is formulated to be compatible with its intended route of administration. Examples of routes of administration include parenteral, e.g. intravenous, intradermal, intramuscular, intra-arterial or subcutaneous administration, and oral administration. Suitable routes of administration are also inhalation and intranasal administration. Another suitable route is rectal administration. Preferably, the administration route is subcutaneous.

When administered subcutaneously, the pharmaceutical composition is preferably injected into well perfused tissue, for example subumbellic tissue, for example subumbellically laterally at the height of the iliac spine.

The pharmaceutical composition may be formulated using any convenient adjuvant and/or physiologically acceptable diluents. The type of formulation depends on the route of administration in a known manner.

In a preferred embodiment, the formulation may be prepared as a tablet, a lozenge, a liquid, gel, a suspension, an emulsion or a solution.

Solutions or Suspensions used for parenteral, in particular subcutaneous, application can include the following components: a sterile diluent such as water for injection, (physiological) saline solution, phosphate buffered saline, fixed oils, polyethylene glycols, glycerine, propylene glycol, or other synthetic solvents; antibacterial agents such as benzyl alcohol or methyl parabens; antioxidants such as ascorbic acid or sodium bisulfate; chelating agents such as ethylenediamine tetraacetic acid (EDTA); buffers such as acetates, citrates, or phosphates and agents for the adjustment of tonicity such as sodium chloride or dextrose. The pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for parenteral administration are injectables. For the preparation of injectables sterile aqueous solutions, dispersions or emulsions are used. Sterile powders for the extemporaneous preparation of sterile injectable solutions or dispersions may also be used. For parenteral administration, suitable carriers include physiological saline, bacteriostatic water, Cremophor® EL (BASF, Parsippany, N.J.), or phosphate buffered saline (PBS). In all cases, the composition must be sterile and should be fluid to the extent that easy syringability exists. It should be stable under the conditions of manufacture and storage and must be preserved against the contaminating action of microorganism such as bacteria and fungi. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganism can be achieved by various antibacterial and antifungal agents, for example, parabens, chlorobutanol, phenol, ascorbic acid, thimerosal, and the like. According to embodiments, isotonic agents, for example, sugars, polyalcohols such as manitol, sorbitol, or sodium chloride in the composition are added. Prolonged absorption of the injectable compositions can be brought about by including in the composition an agent which delays absorption, for example, aluminum monostearate and gelatin.

Sterile injectable solutions can be prepared by incorporating the active compound in the required amount in an appropriate solvent with one or a combination of ingredients enumerated above, as required, followed by sterilization, e.g. by filtration or heat sterilization. Generally, dispersions are prepared by incorporating the active compound into a sterile vehicle which contains a basic dispersion medium and the required other ingredients from those enumerated above. In the case of sterile powders for the preparation of sterile injectable solutions, the preparation is prepared by vacuum drying or freeze-drying, which yields a powder of the active ingredient plus any additional desired ingredient from a previously sterile-filtered solution thereof.

In a further preferred embodiment, the formulation of the present invention is suitable for oral administration. Oral compositions generally include inert diluents or edible carriers. For the purpose of oral therapeutic administration, the active compound can be incorporated into excipients and can be used in the form of tablets, troches, chewie, lozenges, gel caps, soft gel or capsules, e.g. gelatin capsules. Oral compositions can also be prepared using a fluid carrier for use as a mouthwash. Pharmaceutically compatible binding agents or adjuvant materials can be included as part of the composition. The tablets, pills, capsules, troches, lozenges and the like can contain any of the following ingredients, or compounds of a similar nature: a binder such as microcrystalline cellulose, gum tragacanth or gelatin; an excipient such as starch or lactose, a disintegrating agent such as alginic acid, primogel (sodium starch glycolate), or corn starch; a lubricant such as magnesium stearate; a glidant such as colloidal silicon dioxide; a sweetening agent such as sucrose or saccharin.

The formulation of the present invention may include any additional component as desired, as long as such components do not substantially erode the effectiveness of the Ezrin peptide 1. Of course, the additional components are typically pharmaceutically acceptable. Such components may include, for example, thickeners, sweeteners, flavorants, fragrances, additional pharmaceuticals, glycine, mannitol, silicone dioxide, silica gels, binders, vitamins, carriers, such as, for example, glycerin, starches, celluloses, chitins, water, alcohol, and minerals.

Pharmaceutical compositions suitable for inhalation include any formulation that can be converted into an aerosol by means of an inhalation system, including meter dosed inhalers, dry powder inhalers, soft-mist inhalers and nebulizers. In particular, the pharmaceutical compositions for inhalation are suitable for being converted into an aerosol having an particle size of at most 10 µm, in particular at most 5 µm. Suitable compositions include solutions, suspension and also dry powders. Depending on the type of composition, they may contain pharmaceutically acceptable solid or liquid carriers, and/or pharmaceutically acceptable excipients, including water, physiological saline, bacteriostatic water, PBS, amino acids including, leucine, isoleucine, glycine, and methionine; surfactants such as polysorbates, and sugars, including mannitol, lactose, trehalose, raffinose and the like. Particularly suitable are solutions of Ezrin peptide 1 and/or an analogue thereof in physiologic saline. Pharmaceutical compositions suitable for intranasal administration include any formulation mentioned for inhalation, in particular liquid formulations such as solutions of Ezrin peptide 1 and/or an analogue thereof in physiologic saline.

Fillers, carriers, preservatives, and stabilizers, which are usually used by persons skilled in drug delivery technology, may be used as an acceptable carrier or filler for preparation of the provided pharmaceutical compositions. For injections, distilled water or physiologic saline are predominantly used.

Pharmaceutical compositions suitable for rectal administration are in particular suppositories.

It was surprisingly found by the inventors that Ezrin peptide 1 has the surprising property to avoid a critical course of COVID-19 including the much-feared severe acute respiratory distress syndrome. SARS-COV-2 is absolutely foreign to the human organism since it is a novel virus. Thus, the human body has no appropriate antibody response ready when the infection occurs. This means that following the infection a strong immune response in the patient occurs which may be accompanied by a high inflammatory reaction. This may result in a viral lung inflammation in the course of COVID-19 since immune cells migrate into the infected lung tissue and attack the infected lung tissue via cytotoxic immune cells. The lung tissue becomes more and more inflammatory due to the enormous high immunologic defense accompanied by the immigration of the cytotoxic immune cells. This makes the oxygen exchange more and more difficult and may irreversibly damage the lung tissue due to the development of lung fibrosis.

Ezrin peptide 1 is an immune-modulatory tetradecapetide which has shown an anti-viral effect in cell cultures (R.

Ataullakhanov et al.; Antiviral Mechanisms of the drug 'Gepon': Modulation of Cytokine Gene Transcription in a J-96 Human Cell Line. Eksp Klin Gastroenterol. 2005; (1): 14-9, 106). An explanation of the anti-viral effect was that the docking of the virus to the target cell could be prevented. In addition, it was shown in cell cultures that it has an effect on the inflammatory cytokine production and, thus, has an influence on the inflammatory stress. It reduces the production of pro- and inflammatory cytokins (e.g. IL-1, IL-6, TNF-alpha) but induces the synthesis of alpha- and beta interferons. The inventors concluded that due to the modification of the production of inflammatory cytokins it would be possible to modulate the immunologically induced inflammatory reaction which may occur in the course of COVID-19. Thus, the lung inflammation could be downregulated or even be prevented. Due to the anti-inflammatory effect of Ezrin peptide 1 and its analogues, the risk of pulmonary fibrosis as a result of massive cytokine release in lung tissue can be significantly reduced or even be prevented.

Thus, the early administration of Ezrin peptide 1 after a SARS-COV-2 infection is not only successful due to its anti-viral effect but also due to the anti-inflammatory effect for shortening the overall disease duration and preventing the invasion of the disease to the lung and taking a severe course, e.g. by developing ARDS. Even if the disease has already invaded the lung, the Ezrin peptide 1 administration is expected to prevent a progression of this severe complication of COVID-19.

Furthermore, it was found that administration of Ezrin peptide 1 and/or its analogues will cure or at least ameliorate long post-COVID-19 syndrome, also referred to as long COVID. Although the development of post-COVID-19 syndrome can be avoided or at least the risk of a development of post-COVID-19 syndrome or severity thereof is reduced by administration of Ezrin peptide 1 and/or its analogues during the acute phase of COVID-19 infection, amelioration or even cure of long COVID can also be achieved by administration of Ezrin peptide 1 and/or its analogues after the acute infection has subsided, even weeks or month thereafter. In other words, amelioration or even cure of post-COVID-19 syndrome and its pathological symptoms can be achieved by administration of Ezrin peptide 1 and/or its analogues during post-COVID-19 syndrome. For this, Ezrin peptide 1 and/or its analogues will be administered in a dosage as described above, in particular for several days at a dosage in the range of 0.1 and 5 milligrams per day (mg/d), preferably 0.1 to 4 mg/d, more preferably 0.1 to 1 mg/d, especially 0.1 to 0.5 mg/d.

EXAMPLES

Example 1: 69 Year Old Patient risk factors: adipositase, AV block $1^{st}$ grade, hypertonus
Skiing trip to Switzerland (Grindelwald) from March $1^{st}$-$7^{th}$ Course of Disease:

08.03.2020: Loss of taste 09.03.2020: Feeling ill with fatigue and headache 11.03.2020: Same symptoms but fever over 38° C.

12.03.2020: Coronavirus testing; Same symptoms with fever to 39° C., 13.03.2020: Positive test result; persisting symptoms with starting dry cough 14.03.2020: $1^{st}$ Ezrin peptide 1 administration in the evening, persisting symptoms 15.03.2020: $2^{nd}$ Ezrin peptide 1 administration in the morning, increasing symptoms 16.03.2020: $3^{rd}$ Ezrin peptide 1 administration in the morning, increasing symptoms with strong eye pain 17.03.2020: $4^{th}$ Ezrin peptide 1 administration in the morning, increasing symptoms with more cough 18.03.2020: $5^{th}$ Ezrin peptide 1 administration in the morning, significant signs of recovery, no eye pain, decreasing fever 19.03.2020: $6^{th}$ Ezrin peptide 1 administration in the morning, significant signs of recovery, normal body temperature, no fatigue 20.03.2020: $7^{th}$ Ezrin peptide 1 administration in the morning, return of taste, good general condition 21.03.2020: $8^{th}$ Ezrin peptide 1 administration in the morning, no signs of illness anymore Dosage: 2 mg Ezrin peptide 1, dissolved in saline solution, separated into 10 single doses (à 0.2 mg), 1 single dose per subcutaneous administration daily Surprisingly, the severity of symptoms after administration was significantly lower than one would have expected in a patient of this risk group. The course of the disease was also significantly shorter compared to the course of the disease expected for patients of this risk group. Severe complications such as fibrosis of the lungs did not occur.

Example 2: 64 Year Old Male Patient

Risk factors: hypertonus, asthma, COPD, hyperchlosterinaemia

Permanent medication:
Candesartan 8 mg
Foster (beclometason dipropionate, formoterol fumarate dihydrate)
Simvastatin Dosage: Six single doses à 2 mg Ezrin peptide 1, dissolved in saline solution and administered subcutaneously (s.c.).

Course of Disease:

23.04.2020: First occurrence of fever, 38.4° C.;

24.04.2020: Severe clinical symptoms with high fever above 39.0° C., nausea, loss of taste, respiratory distress, dry cough, severe headache; Corona-PCR was prepared with positive result for SARS-COV-2, First Ezrin peptide 1, 2 mg subcutaneous (s.c.) in the evening;

25.04.2020: In the morning second dose of Ezrin peptide 1, 2 mg s.c.; body temperature dropped to 37.5° C. in the morning, still general weakness, shortness of breath, cough, loss of appetite, in the evening body temperature again 39.0° C.;

26.04.2020: Third administration of Ezrin peptide 1, 2 mg s.c.; Still loss of appetite, slight cough, in the evening body temperature still 37.5° C.;

27.04.2020: Fourth dose of Ezrin peptide 1, 2 mg s.c.; Slight cough, slight headache, body temperature 37.4° C.;

28.04.2020: Fifth administration of Ezrin peptide 1, 2 mg s.c.; Only slight pain of touching the scalp, still slight weakness, body temperature 37.3° C.;

30.04.2020: Sixth administration of Ezrin peptide 1, 2 mg s.c.; Significant improvement of clinical symptoms, normal temperature, macrohaematuria (inconspicuous urological consultation), CRP level >100 mg/l, a CT of the thorax was carried out because of suspected pneumonia;

01. to 04.05.2020: antibiotic coverage due to increased CRP level, taste completely returned, no more cough, no more fever, clinical well-being.

Example 3: 79 Year Old Male Patient

Risk factor/pre-existing illnesses: COPD, Diabetes mellitus Typ2, 2 artificial heart valves, Apoplexia in 2018

Dosage: Single doses of 2 mg Ezrin peptide 1, dissolved in saline solution and administered subcutaneously (s.c.) on Dec. 23, 2020 followed by 0.2 mg/d Ezrin peptide 1 (single doses, s.c.) for four days.

Course of Disease:

First symptoms: Beginning of December 2020: Cough, loss of sense of smell and taste;

Continuously worsening of cough, fatigue and loss of appetite, shortness of breath since 18.12.2020;

Positive Antigen-Test (Lateral-flow-test) 22.12.2020, positive PCR test for SARS-Cov2 on 23.12.2020;

23.12.2020 begin of HEP-1 therapy with 2 mg/d for two days followed by 0.2 mg/d for four (4) days;

25.12.2020 significant improvement of cough and general condition;

No further symptoms after completion of HEP-1 therapy.

Example 4: 49 Year Old Female Patient

Risk factor/pre-existing illnesses: Hypertension

Dosage: Single doses of 2 mg/d Ezrin peptide 1, dissolved in saline solution and administered subcutaneously (s.c.) for 2 days, followed by 0.2 mg/d Ezrin peptide 1 (single doses, s.c.) for four (4) days.

Course of Disease:

First symptoms: 19.12.2020 Severe cough, fatigue, chills;

Further symptoms: 21.12.2020 diarrhoea, thoracic pain, angina pectoris, shortness of breath;

Positive Antigen-Test (Lateral-flow-test) 21.12.2020, positive PCR test for SARS-Cov2 on 23.12.2020;

23.12.2020 begin of HEP-1 therapy with 2 mg/d for two days followed by 0.2 mg/d for four days;

25.12.2020 significant improvement of cough and general condition;

No further symptoms after completion of HEP-1 therapy.

Example 5: 53 Year Old Male Patient

Risk factor/pre-existing illnesses: Hypertension

Initial dosage: Single doses of 2 mg/d Ezrin peptide 1, dissolved in saline solution and administered subcutaneously (s.c.) for 2 days, followed by 0.2 mg/d Ezrin peptide 1 (single doses, s.c.) for four days.

Subsequent dosage: 0.2 mg/d Ezrin peptide 1 (single doses, s.c.) for fourteen (14) days.

Course of Disease:

First symptoms: 23.12.2020 Severe cough and rhinitis, limb pains, sore throat, loss of sense of smell and taste, angina pectoris, fatigue, chills;

23.12.2020 begin of HEP-1 therapy with 2 mg/d (single dose) for two days followed by 0.2 mg/d for four days;

26.12.2020 significant improvement of symptoms;

28.12.2020: PCR-Re test for SARS-Cov2 still positive;

No further symptoms after completion of HEP-1 therapy until 13.01.2021, then severe shortness of breath;

15.01.2021: Administration of 0.2 mg/d Ezrin peptide 1 (single dose) for fourteen (14) days;

No further shortness of breath after completion of HEP-1 therapy.

Example 6: 68 Year Old Female Patient

Risk factor/pre-existing illnesses: unknown
Dosage: Single doses of 0.2 mg/d Ezrin peptide 1, dissolved in saline solution and administered subcutaneously (s.c.) for ten (10) days.
Course of Disease:
First symptoms: 09.12.2020 fever, cough, headache, shortness of breath and fatigue;
Positive PCR test for SARS-Cov2 on 10.12.2020;
10.12.2020 begin of HEP-1 therapy with 0.2 mg/d for ten (10) days;
14.12.2020 significant improvement of symptoms;
20.12.2020 complete recovery of symptoms.

---

The invention claimed is:

1. A method of treating COVID-19 or post COVID-19 syndrome in a subject, comprising administering to the subject Ezrin peptide 1, wherein the Ezrin peptide 1 consists of the amino acid sequence NH2_Thr-Glu-Lys-Lys-Arg-Arg-Glu-Thr-Val-Glu-Arg-Glu-Lys-Glu_COOH (SEQ ID NO:1).

2. The method of claim 1, wherein the Ezrin peptide 1 is dissolved in saline solution for subcutaneous administration.

3. The method of claim 1, wherein the Ezrin peptide 1 is formulated for oral administration.

4. The method of claim 1, wherein the Ezrin peptide 1 is formulated for inhalation or for intranasal administration.

5. The method of claim 1, wherein the Ezrin peptide 1 is administered daily.

6. The method of claim 1, wherein the subject is a human tested positive for SARS-COV-2 or suspected of being infected with SARS-COV-2.

7. The method of claim 1, wherein the Ezrin peptide 1 is administered in a pharmaceutical composition comprising the Ezrin peptide 1 and a pharmaceutically acceptable carrier.

8. The method of claim 7, wherein the composition is formulated either for subcutaneous administration, oral administration, inhalation or intranasal administration.

9. A method of treating COVID-19 or post COVID-19 syndrome in a subject, comprising administering to the subject an analogue of Ezrin peptide 1, wherein the analogue consists of the formula (I)

(I)
(SEQ ID NO: 5)
NH2_X1-Glu-Lys-Lys-Arg-Arg-Glu-Thr-Val-Glu-Arg-Glu-X2-$\overline{X3}$_COOH where X1, X2 and X3 are identical or different and are non-polar amino acid residues.

10. The method of claim 9, wherein X1, X2 and X3 are identical and glycine residues.

11. The method of claim 9, wherein the analogue is dissolved in saline solution for subcutaneous administration.

12. The method of claim 9, wherein the analogue is formulated for oral administration.

13. The method of claim 9, wherein the analogue is formulated for inhalation or intranasal administration.

14. The method of claim 9, wherein the analogue is administered daily.

15. The method of claim 9, wherein the subject is a human tested positive for SARS-COV-2 or suspected of being infected with SARS-COV-2.

16. The method of claim 9, further comprising administering Ezrin peptide 1 consisting of the amino acid sequence NH2 Thr-Glu-Lys-Lys-Arg-Arg-Glu-Thr-Val-Glu-Arg-Glu-Lys-Glu COOH (SEQ ID NO: 1) in combination with the analogue of Ezrin peptide 1.

17. The method of claim 9, wherein the analogue of Ezrin peptide 1 is administered in a pharmaceutical composition comprising the analogue of Ezrin peptide 1, or in combination with Ezrin peptide 1 consisting of the amino acid sequence NH2 Thr-Glu-Lys-Lys-Arg-Arg-Glu-Thr-Val-Glu-Arg-Glu-Lys-Glu COOH (SEQ ID NO: 1), and a pharmaceutically acceptable carrier.

18. The method of claim 9, where X1, X2 and X3 are each individually selected from the group of amino acid residues consisting of glycine, alanine, valine, leucine, methionine, isoleucine, proline, phenylalanine, and tryptophan.

* * * * *

SEQUENCE LISTING

```
<160> NUMBER OF SEQ ID NOS: 6

<210> SEQ ID NO 1
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Tetradecapeptide of human Ezrin

<400> SEQUENCE: 1

Thr Glu Lys Lys Arg Arg Glu Thr Val Glu Arg Glu Lys Glu
1               5                   10

<210> SEQ ID NO 2
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Ezrin derived polypeptide

<400> SEQUENCE: 2

Gly Glu Lys Lys Arg Arg Glu Thr Val Glu Arg Glu Gly Gly
1               5                   10

<210> SEQ ID NO 3
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Thr Glu Lys Lys Arg Arg Glu Thr Val Glu Arg Lys Glu Lys Glu
1               5                   10                  15

<210> SEQ ID NO 4
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Gly Glu Lys Lys Arg Arg Glu Thr Val Glu Arg Lys Glu Gly Gly
1               5                   10                  15
```

-continued

```
<210> SEQ ID NO 5
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Non-polar amino acid residue
<220> FEATURE:
<221> NAME/KEY: MOD_RES
<222> LOCATION: (13)..(13)
<223> OTHER INFORMATION: Non-polar amino acid residue
<220> FEATURE:
<221> NAME/KEY: MOD_RES
<222> LOCATION: (14)..(14)
<223> OTHER INFORMATION: Non-polar amino acid residue

<400> SEQUENCE: 5

Xaa Glu Lys Lys Arg Arg Glu Thr Val Glu Arg Glu Xaa Xaa
1               5                   10

<210> SEQ ID NO 6
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Thr Glu Lys Lys Arg Arg Glu Thr Val Glu Arg Glu Lys Glu
1               5                   10
```